United States Patent [19]

Dabelstein et al.

[11] Patent Number: 4,693,601
[45] Date of Patent: Sep. 15, 1987

[54] LIGHT SCANNING DEVICE FOR DETERMINING THE CONDITION OF A SURFACE WITH A LIGHT CONCENTRATOR

[75] Inventors: Klaus Dabelstein, Pöcking/Starnberg; Christian Skrobol, Inning, both of Fed. Rep. of Germany

[73] Assignee: Erwin Sick GmbH Optik-Elektronik, Waldkirch, Fed. Rep. of Germany

[21] Appl. No.: 861,017

[22] Filed: May 8, 1986

[30] Foreign Application Priority Data

May 24, 1985 [DE] Fed. Rep. of Germany ....... 3518832

[51] Int. Cl.$^4$ ...................... G01N 21/89; G01N 21/47
[52] U.S. Cl. .................................... 356/237; 356/431; 356/446
[58] Field of Search ............... 356/237, 429, 430, 431, 356/446; 250/571, 572; 350/628, 630

[56] References Cited

U.S. PATENT DOCUMENTS 4,523,853 6/1985 Rosenbladt et al. ................ 356/446

Primary Examiner—Vincent P. McGraw
Attorney, Agent, or Firm—Townsend & Townsend

[57] ABSTRACT

A light scanning device for determining the condition of a surface has an optical system which concentrates light beams leaving a scanning line in a specific direction at a concentration zone (16'). A light concentrator (11) with a light entry surface (12) and a desired light exit surface (13) arranged parallel thereto are arranged at the location of the concentration zone (16'). Convexly curved side surfaces (15) which are mirrored at the outside are present between the light entry surface (12) and the desired light exit surface (13) and ensure that light entering alongside a dark field stop (14) all falls onto a photomultiplier which adjoins the desired light exit surface (13) (FIG. 5).

14 Claims, 8 Drawing Figures

LIGHT SCANNING DEVICE FOR DETERMINING THE CONDITION OF A SURFACE WITH A LIGHT CONCENTRATOR

The invention relates to a light scanning device for determining the condition of a surface. Known apparatus of this kind comprises means for forming a scanning line of the surface of an article and an optical system for concentrating, at a point-like concentration zone, all the light beams which lie in a plane extending parallel to the scanning line and which leave the surface, depending on the surface condition, either in a specific direction corresponding to a normal reflection, or in a direction which deviates somewhat from this as a result of surface faults. The point-like concentration zone is located, depending on whether the light beams have the normal direction or deviate in angle somewhat therefrom, either at a normal position on the light entry surface of a transparent light concentrator, or displaced somewhat relative thereto in the direction of the scanning line. The light concentrator has outer mirrored side surface and tapers away from the concentration zone to a desired light exit surface where an areal photoconverter, in particular a photomultiplier is arranged. A dark field stop is arranged at the normal position for the light concentrator, and preferably also in a small angular range about this normal position. The stop permits only a light beams which leave the surface above a predetermined angle of deviation relative to the normal direction to enter into the light concentrator.

Such light scanning devices are for example used for the surface inspection of specularly reflecting material such as sheet metal. In this arrangement a scanning beam is directed by means of a mirror wheel illuminated by a laser beam obliquely onto a web of metal in order to generate a sharply bundled scanning light bead. The scanning light bead sweeps over the web cyclically, preferably transverse to its direction of movement. In this manner the web is scanned linewise. The light reflected from the web is picked-up by a cylindrical lens arranged close to the surface parallel to the line of the light generated by the scanning light bead and directed to a spherical, parabolic or cylindrical, in particular strip-like concave mirror which concentrates all the received reflected scanning beams at a single point-like concentration zone. This concentration zone represents the image of the surface of the mirror wheel. In place of the image forming concave mirror one could however also use a corresponding lens of strip-like shape.

A photoelectric converter arrangement, which mainly consists of a photomultiplier, can be arranged in the concentration zone. It is however problematic with this arrangement that on the occurrence of faults at the surface the concentration zone wanders from its normal position in the direction of the line of light in the one or other direction and broadens out during this movement in the manner of a caustic. This deflection of the concentration zone preferably amounts of 5 cm or in angular terms to about 1.5° so that a photo-receiving surface with such a large areal extent must be provided, above all in the direction of the line and this can normally not be made available by a photomultiplier.

For this reason one has already placed a transparent light concentrator between the concentration zone and the receiving surface of the photomultiplier with the light concentrator being constructed in the manner of a conically tapering prism with outer mirrored side surfaces and having a relatively large light entry surface and a light exit surface which is approximately half as large. With this arrangement the light entry surface is dimensioned so that it is sufficiently large in the direction of the line of light that it detects all the light beams which fall within an angle of $+1.7°$ to $+0.6°$ to the concentration zone and allows them to pass by reflection at the side surfaces of the light concentrator as fully as possible to the reduced light exit surface where the photomultiplier is arranged.

The principal object underlying the present invention is now to provide a light scanning device of the initially named kind wherein, taking account of the natural fundamental limits, the light concentration in the light concentrator is optimised in such a way that the useful angular range within which all incident light beams also pass to the desired light exit surface reaches an absolute maximum value.

In order to satisfy this object the invention provides that externally mirrored side surfaces of the tapering light concentrator are increasingly convexly curved in the direction away from the entry surface in such a way that at least some of the light beams which fall in the range of the dark field stop would fall, if the dark field stop were imagined to be missing, on the convexly curved side surfaces at angles so steep that they would be reflected backwardly in the light concentrator without reaching the desired light exit surface; and that all the light beams which enter alongside the dark field stop into the light entry surface of the light concentrator impinge on the mirrored side surfaces at such shallow angles that they all reach the desired light exit surface.

The base thought underlying the invention thus lies in the concept of so shaping the side surfaces of the light concentrator that the light beams which are incident in the region covered by the dark surface would, in the event that the dark field stop were not present, be at least partly reflected in such a way that they would impinge for a second time on the opposite side surface, and indeed at such a steep angle that they would be reflected there backwardly away from the desired light exit surface, and would thus be lost for exploitation at the photomultiplier.

However, because of the actual arrangement of the dark field stop at the central region of the light entry surface this is not disadvantageous because these light beams would in any event be kept away from the photomultiplier by the dark field stop because it is not the normally reflected beam but rather the beams which originate from faults which are intended to influence the measurement. Instead of this the invention makes it possible, taking account of and keeping within the fundamental physical limits to select the useful angular range to be substantially larger than was previously possible with light concentrators. If, for example, the dark field stop covers over an angular range of approximately 1° than a useful angular range from 1° to 1.7° can be provided on each side of it, with all the light beams which enter within this angular range into the light entry surface of the light concentrator being able to pass by reflection at the mirrored surface to the desired light exit surface where the photomultiplier is arranged, without light being reflected backwardly through incidence at an angle which is too steep. The physical requirements can however be maintained because conditions are achieved in accordance with the invention for the light beams which fall on the dark field stop which would lead to partial backward reflection of these light beams at the side surfaces if these light beams were not covered over by the dark field stop. The arrangement is preferably such that the light entry surface extends, for light beams emerging from the surface in the specified direction, perpendicular to the central beam.

Furthermore, the desired light exit surface should extend parallel to the light entry surface.

Moreover, it is expedient if the dark field stop 14 is arranged symmetrically at the center of the light entry surface of the light concentrator.

In order to provide symmetrical angular ranges for fault detection on both sides of the central beam the curved side surfaces should extend symmetrically to the central beam.

It is particularly advantageous if the curved side surfaces have the shape of a parabola translated parallel to its plane with the apex lying substantially behind the desired light exit surface.

As a result of the design of the invention it is straightforwardly possible to release light concentrators in which the ratio of the light entry surface to the desired light exit surface amounts to approximately 2:1.

The light concentrator of the invention is thus a structure equivalent to a body of revolution the sections of which parallel to the plane of the plurality of light beams are all the same. The convexly curved side surfaces are thus surfaces curved in one plane which are substantially simpler to produce than spherically curved surfaces.

The ideal detection of larger exploitable angular ranges is achieved when the side surfaces follow the function $$y = \frac{a \cdot x^2}{1 + \sqrt{1 - (b + 1) \cdot a^2 \cdot x^2}}$$

in which a and b are constants with a preferably lying between +0.012 and +0.14 and b preferably lying between −0.3 and −1.0. The value a is in particular approximately +0.05 and the value b approximately −0.9.

The invention will now be described by way of example and with reference to the drawings which show.

In all figures the same reference numerals are used to designate the same parts.

Figure 1:
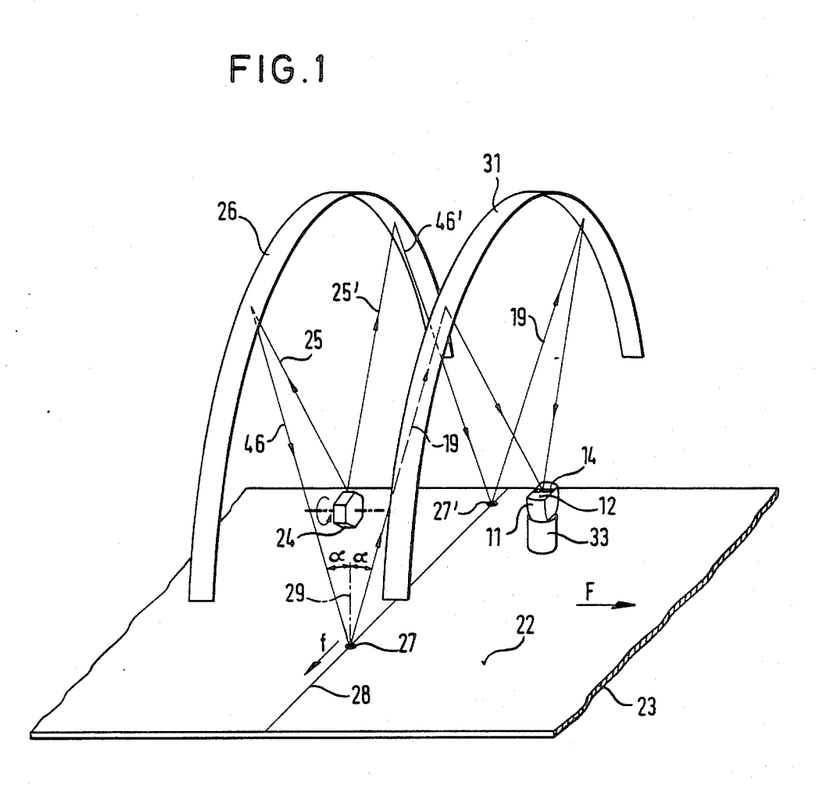
FIG. 1 a purely schematic perspective illustration of a light scanning device for determining the condition of a surface in accordance with the invention, FIG. 2 a schematic plan view of the reception beam path of the light scanning device of FIG. 1 with the reception beam path folded into a single plane, FIG. 3 an enlarged view of the section III in FIG. 2, FIG. 4 a view analogous to FIG. 2 with the reflected light beams being deflected by the extreme angle of 1.7° by a corresponding surface condition, FIG. 5 the section V in FIG. 4 to an enlarged scale, FIG. 6 a view analogous to FIGS. 3 and 5 for that angle of deflection of the light beams beyond which all the light beams entering into the light concentrator reach the desired light exit surface, with the deflection angle amounting to 0.6°, FIG. 7 an analogous view for a deflection angle of 0.2°, and FIG. 8 an analogous view for a deflection angle of 1°.

As seen in FIG. 1 a steel web or continuous steel sheet 23 is moved continuously in the direction of the arrow F beneath a light scanning device in accordance with the invention. A laser light beam 25 is directed by means of a mirror wheel 24 illuminated, in non-illustrated manner, by a laser onto a strip-like concave mirror 26 which extends in arch-like manner over the web 23 transverse to its direction of movement F. On rotating the mirror wheel the laser beams 25 moves in a sector over the strip-like concave mirror and, as a result, reaches, for example, also the position shown at 25'. On rotation of the mirror wheel 24 scanning beams 46, 46' are generated by the concave mirror 26 which are displaced parallel to themselves and which generate a scanning light bead 27 and 27' respectively on the surface 22 of the web 23. In this way the scanning light bead periodically sweeps over or scans the web in the direction of the arrow f, so that as a whole a streak of light or line of light 28 arises. In this way, as a result of the continuous movement of the web in the direction of the arrow F, linewise scanning of the surface 22 by means of the light bead 27 is ensured.

The light transmitting arrangement including the mirror wheel 24 and the concave mirror 26 is arranged obliquely to the surface 22 of the web in such a way that the scanning beams 46, 46' are incident on the web at an angle α relative to the perpendicular 29 to the surface 22.

A cylindrical lens (not shown) is preferably arranged in the path of the scanning beams 46, 46' close to the surface 22.

Figure 2:
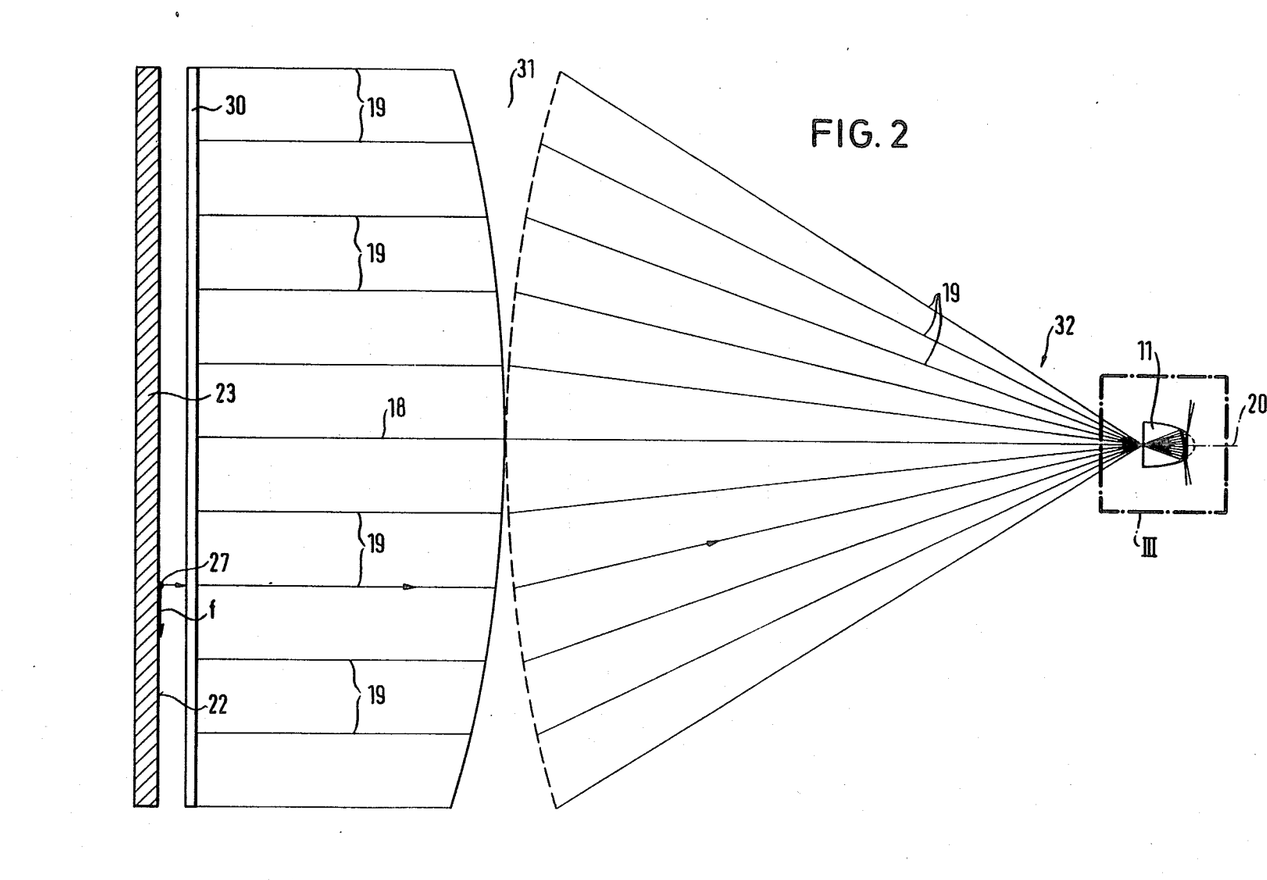

The light beams which are reflected from the surface 22 at the angle of reflection α reach, in accordance with FIGS. 1 and 2, preferably after passing through a cylindrical lens 30 indicated in FIG. 2, a further strip-like mirror 31. Ship-like concave mirror 31 collects the reflected light beams 19 which are displaced parallel to themselves onto the light entry surface 12 of a light concentrator 11 in accordance with the invention. The light concentrator 11 is a transparent block the flat-like entry surface 12 of which extends perpendicular to the central beam 18 of the fan of light 32 formed by the totality of the reflected light beams 19. At its lower or rear end the light concentrator 11 has a light exit surface 13 which extends parallel to the light entry surface 12 with a photomultiplier 33 being adhered to the desired light exit surface 13 or coupled thereto via a liquid. The photomultiplier receives all the light which impinges onto the desired light exit surface 13 and transmits, in manner not shown, an electrical signal proportional to the incident quantity of light (light flux) to an electronic processing circuit. It is thus important that the photomultiplier 33 is coupled in an optically problemfree manner without one or more boundary surfaces to the light concentrator 11. This coupling can be achieved by means of adhesive or through an oil.

Figure 3:
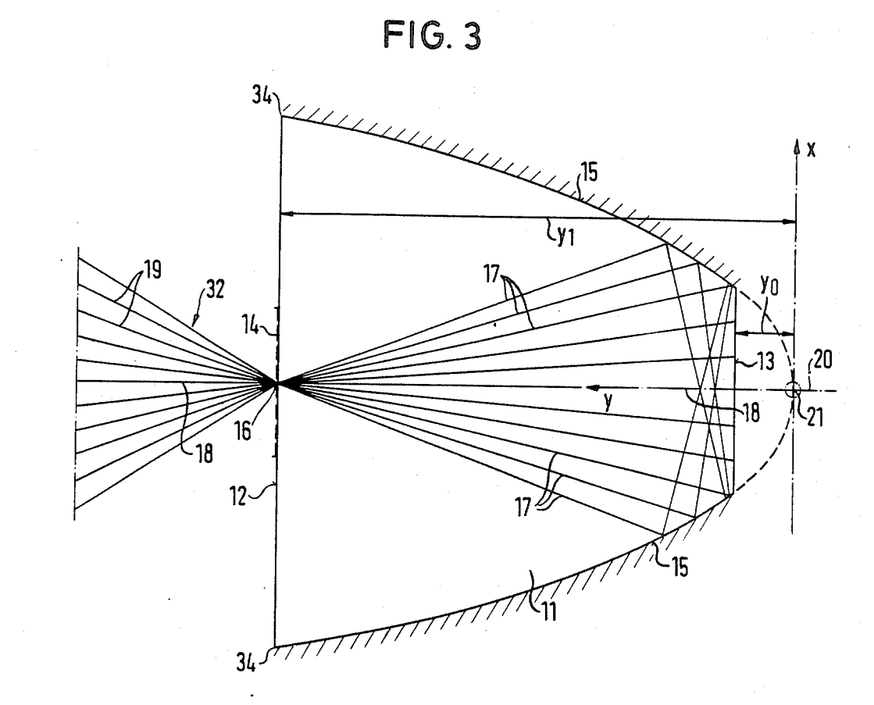

As seen in FIGS. 1 and 3 the light entry surface 12 is covered over in the central region by a dark field diaphragm or stop 14, which is only shown in broken lines in FIG. 3, so that the light beams 19 reflected by normally reflecting surface 22 are incident on the dark field stop 14 and are prevented by the latter from entering into the light concentrator 11. The light beams 19 are concentrated in accordance with FIG. 3 at a point-like concentration region 16 at the center of the dark field stop 40.

The light concentrator 11 of the invention has, in the sideview of FIG. 3, substantially the shape of a parabola which has been cut off at both ends perpendicular to its central axis 20, whereby the light entry surface 12 and the light exit surface 13 are formed. Side surfaces 15 which are increasingly convexly curved and mirrored at the outside extend away from the two ends 34 of the light entry surface 12 at an angle of somewhat less than 90°. The curved side surface 15 terminate at a distance $y_o$ from the apex 21 and merge there into the light exit surface 13 which extends parallel to the light entry surface 12. The photomultiplier 33, which is not shown in FIG. 3 adjoins the desired light entry surface 13. The distance of the light entry surface 12 from the apex 21 of the convexly curved edge surfaces 25 is designated by $y_1$ in FIG. 3.

A cartesian x-y coordinate system is entered in chain-dotted lines in FIG. 3 with its orgin O at the location of the apex 21.

In accordance with the invention the edge surfaces 15 in this coordinate system are shaped in accordance with the following function:

$$y = \frac{a \cdot x^2}{1 + \sqrt{1 - (b+1) \cdot a^2 \cdot x^2}}$$

The parameter a is approximately +0.5, the parameter b approximately −0.9. This is thus an ellipsoidal function. The ratio $y_0$ and $y_1$ amount in the illustrated embodiment to approximately 1.2 and 11.2 respectively.

The values $y_o$ and $y_1$ is, in accordance with the invention, expediently approximately 1:10. The desired light exit surface 13 is matched to the effective light pick-up surface of a customary photomultiplier 33. The extent of the desired light exit surface 13 in the x-direction is thus approximately 4.5 cm and approximately 4.5 cm perpendicular thereto.

It is now assumed that the dark field stop 14 indicated in broken lines in FIG. 3 has been omitted so that the light beams 18, 19 which come together at the concentration zone 16 can enter in the illustrated manner into the light concentrator 11. As a result of the design, in accordance with the invention, of the convexly curved mirrored edge surfaces 15 and the light beams 17 fall on the mirrored side surfaces 15 at such a steep angle that none of these light beams 17 reach the desired light exit surface 13. On the contrary these light beams 17 are reflected so that them impinge for a second time on the opposite side surface 15, and indeed at an angle such that they are reflected back from there away from the desired light exit surface 13 in the direction of the light entry surface 12. The corresponding light would thus be lost for detection by the photomultiplier coupled in light-tight manner behind the desired light exit surface 13. Since, however, the dark field stop 14 is actually provided the relevant light beams are in any event not evaluated for the measurement so that the above described characteristic of the light concentrator of the invention does not have any disadvantages effects, but does make it possible to convey light beams which are incident further outwardly to the desired light exit surface 13 without losses.

Figure 4:
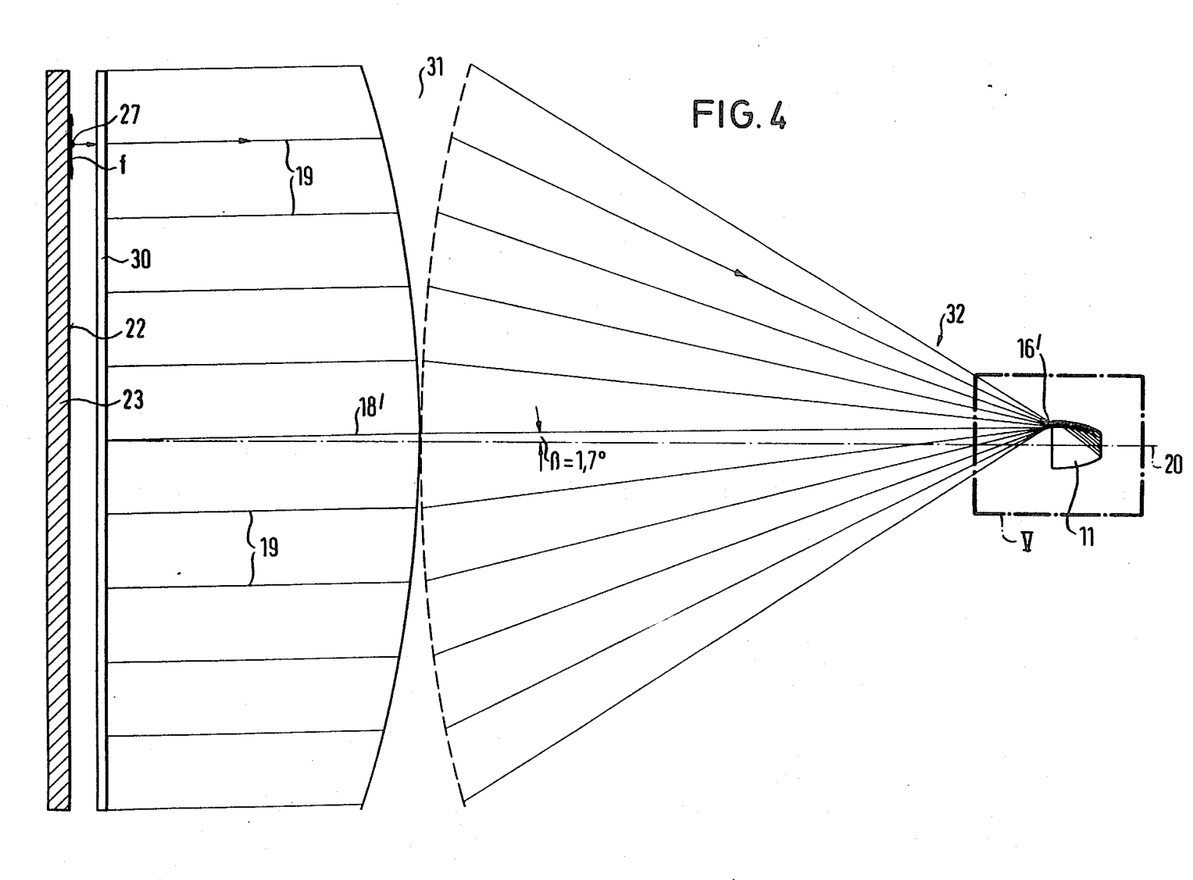
Figure 5:
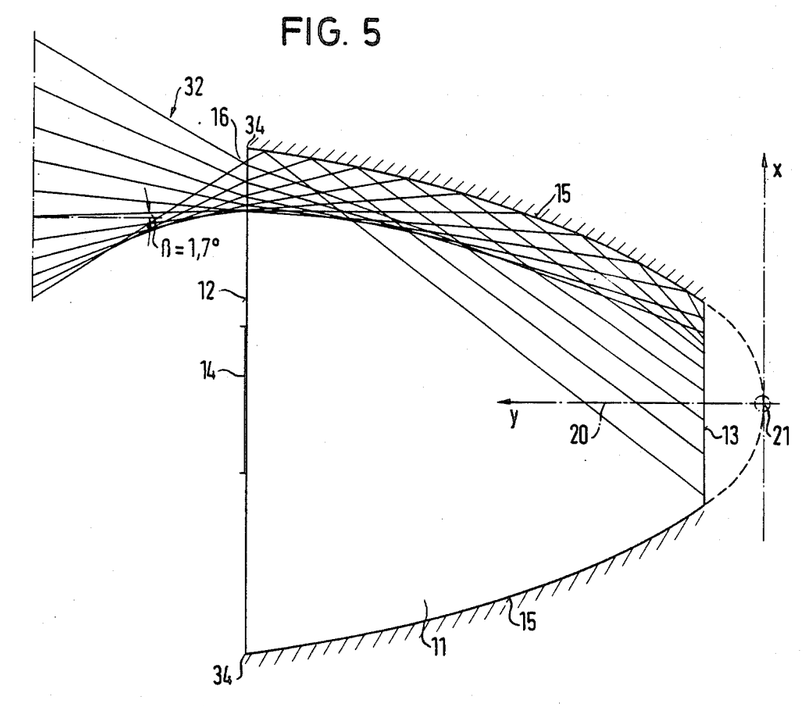

In the illustration of FIGS. 4 and 5 it is assumed that the light beams 19 reflected from the surface 22 of the web 23 are deflected in an extreme manner as a result of a surface fault or tilting of the web in the direction of the line of light 28 (FIG. 1 through an angle $\beta$ which is shown in FIG. 4 solely for the central beam 18 and amounts, in the embodiment, to 1.7°. As a result of this circumstance the concentration region 16 is displaced, in particular as seen in FIG. 5, up to the upper outermost edge of the light entry surface 12 whereby the entire light fan 32 can enter into the interior of the light concentrator 11. In so far as the incident light does not directly reach the desired light exit surface 13 it is completely reflected at the upper mirrored side surface 15 at an angle which is so shallow that it passes after reflection to the desired light exit surface 13 and is thus fully detected by the photomultiplier 33 (FIG. 1). The detection of such a large angle of deflection of 1.7° is only possible as a result of the construction of the side surfaces 15 in accordance with the invention, through which the condition for the incidence of the light beams which are captured by the dark field diaphragm 14 on the desired light exit surface 13 consciously not satisfied.

Figure 6:
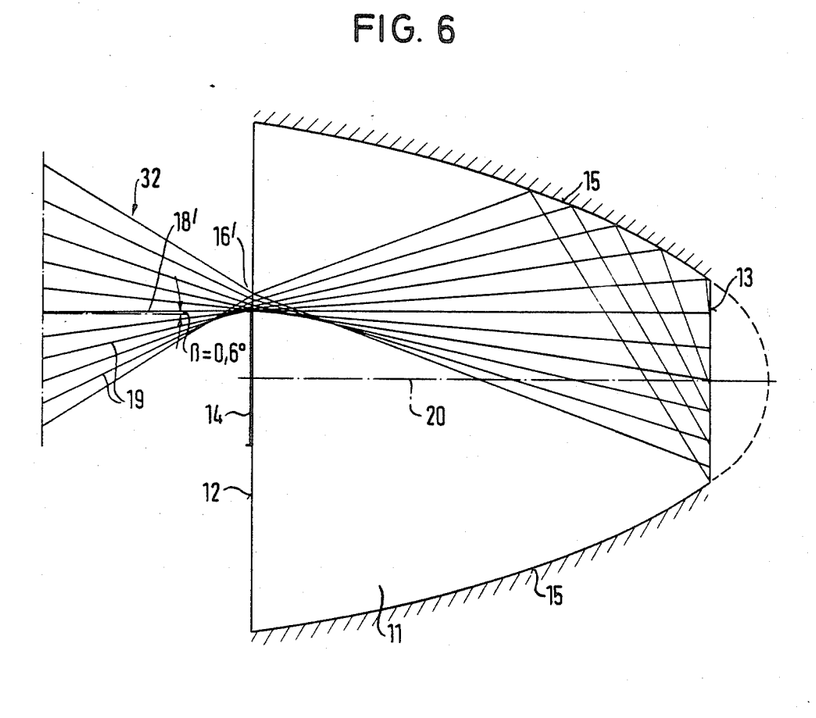
Figure 7:
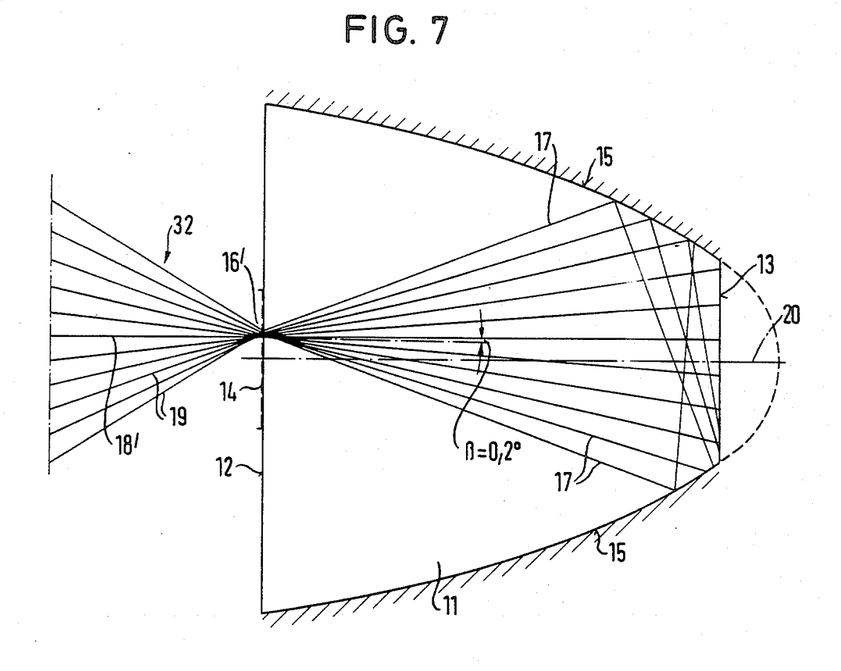

FIG. 6 shows the conditions for an angle of deflection $\beta$ of all the emergent light beams 19° of 0.6°. At this angle the concentration zone 16' just passes alongside the dark field stop 14 so that all the light just reaches the desired light exit surface. For the sake of comparison FIG. 7 illustrates the case in which the angle of deflection $\beta$ amount to 0.2°, the concentration zone 16' is thus located inside the dark field stop 14 which is here again only illustrated in broken lines. One can see that in this case some of the light beams 17 which would enter into the light concentrator 11 if the dark field stop 14 were omitted do not reach the desired light exit surface 13 but are instead reflected back in the direction away from the desired light exit surface 13 at one of the edge surfaces 15. Only above the angle of deflection $\beta$ illustrated in FIG. 6 of approximately 0.6°, precisely 0.57°, is the condition satisfied that all the light beams entering into the light concentrator pass to the desired light exit surface 13.

Figure 8:
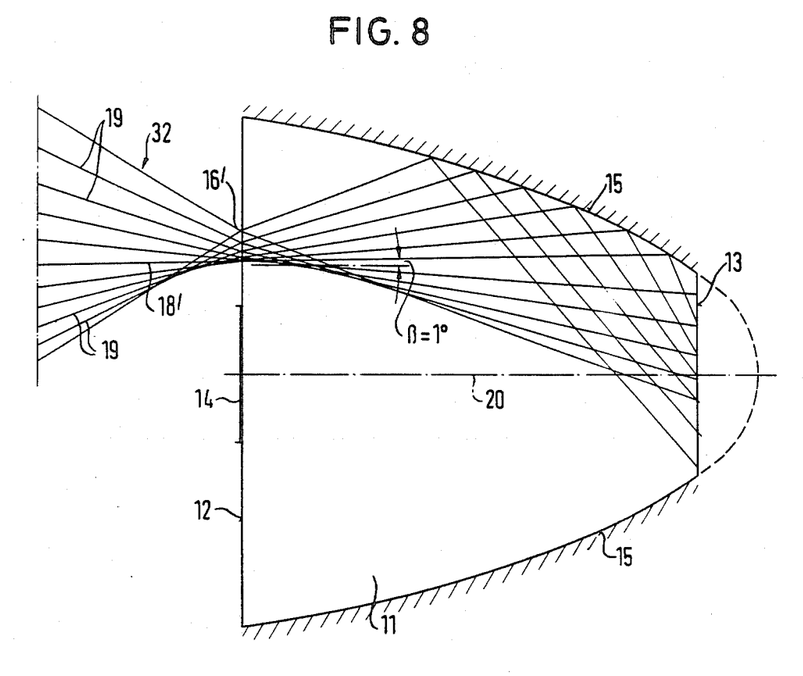

FIG. 8 illustrates finally an intermediate deflection angle $\beta$ of 1° in order to show that also in this case all the light beams entering from the concentration zone 16' into the light concentrator 11 reach the desired light exit surface 13.

Accordingly, a useful angular range $\Delta\beta$ of 0.6° to 1.7° is provided on both sides of the dark field stop 14 which itself takes up an angular range of approximately 1.2°. If one combines the two usable angular ranges on both sides of the dark field stop 14 then a total useful angular range of approximately 2.2° results which however effectively extends, as a result of the blending out of the central part in the region of the dark field stop which is not taken into account from −1.7° to +1.7°, i.e. light beams in the outer parts of a total angle range of 3.4° are fully directed to the narrowed desired light exit surface 14.

We claim:

1. A light scanning device for determining the condition of a surface comprising means for forming a scanning line on the surface of an article and an optical system for concentrating, at a point-like concentration zone, all the light beams which lie in a plane extending parallel to the scanning line and which leave the surface, depending on the surface condition, which in a specific direction corresponding to a normal reflection, or in a direction which deviates somewhat from this as a result of surface faults; wherein said point-like concentration zone is located, depending on whether the light beams have the normal direction or deviate in angle somewhat therefrom, either at a normal position on the light entry surface of a transparent light concentrator or displaced somewhat relative thereto in the direction of the light streak; wherein the light concentrator has outer mirrored side surfaces and tapers away from the concentration zone to a desired light exit surface where an areal photoconverter, in particular a photomultiplier is arranged; and wherein a dark field stop is arranged at the normal position for the light concentrator and preferably also in a small angular range about this normal position, said stop permitting only light beams which leave the surface above a predetermined angle of deviation relative to the normal direction to enter into the light concentrator, characterised in that the externally mirrored side surfaces (15) of the tapering light concentrator (11) are increasingly convexly curved in the direction away from the light entry surface in such a way that at least some (17) of the light beams which fall in the range of the dark field stop would fall, if the dark field stop were imagined to the missing, on the convexly curved side surfaces (15) at angles so steep that they would be reflected backwardly in the light concentrator without reaching the desired light exit surface (13); and in that all the light beams which enter alongside the dark field stop (14) into the light entry surface (12) of the light concentrator (11) impinge on the mirrored side surfaces (15) at such shallow angles that they all reach the desired light exit surface (13).

2. A light scanning device in accordance with claim 1, characterised in that the scanning line is generated by a cyclically moved light head.

3. A light scanning device in accordance with claim 1, characterised in that the light entry surface (12) extends, with light beams (19) which emerge from the surface in the specified direction, perpendicular to the central beam (18).

4. A light scanning device in accordance with claim 1, characterised in that the desired light exit surface (13) extends parallel to the light entry surface (12).

5. A light scanning device in accordance with claim 1, characterised in that the dark field diaphragm (14) is arranged symmetrically at the center of the light entry surface (12) of the light concentrator (11).

6. A light scanning device in accordance with claim 1, characterised in that the curved surfaces (15) extend symmetrically to the central beam (18).

7. A light scanning in accordance with claim 1, characterised in that the curved side surfaces (15) have the shape of a parabola translated parallel to its plane with the apex (21) lying substantially behind the desired light exit surface (13).

8. A light scanning device in accordance with claim 1, characterised in that the ratio of the light entry surface (12) to the light exit surface (13) amounts to approximately 2:1.

9. A light scanning device in accordance with claim 1, characterised in that the light concentrator (11) is a curved structure, the sections of which parrallel to the plane of the plurality of light beams are all identical.

10. A light scanning device in accordance with claim 1, characterised in that the side surface (15) follow the function $$y = \frac{a \cdot x^2}{1 + \sqrt{1 - (b + 1) \cdot a^2 \cdot x^2}}$$

where a and b are constants.

11. A light scanning device in accordance with claim 10, characterised in that a lies between ±0.012 and ±0.14 and is in particularly approximately ±0.5.

12. A light scanning device in accordance with claim 10, characterised in that b lies between −0.3 and −1.0 and is in particular approximately 0.9.

13. A light scanning device in accordance with claim 1, characterised in that the dark field diaphragm (14) covers an angular range of the light beams (18, 19) which leave the surface (22) of 1°.

14. A light scanning device in accordance with claim 1, characterised in that the useful angular range outside of the dark field diaphragm (14) on each side lies between 1° and 1.7° relative to the normal direction.

* * * * *